United States Patent
Delhomme et al.

(10) Patent No.: US 9,952,185 B1
(45) Date of Patent: Apr. 24, 2018

(54) METHOD OF CALIBRATING A PHASED ARRAY ULTRASONIC SYSTEM WITHOUT KNOWN TEST OBJECT SOUND SPEED

(71) Applicants: Antoine Delhomme, Versailles (FR); Benoit Lepage, Quebec (CA)

(72) Inventors: Antoine Delhomme, Versailles (FR); Benoit Lepage, Quebec (CA)

(73) Assignee: Olympus Scientific Solutions America, Waltham, MA (US)

(*) Notice: Subject to any disclaimer, the term of this patent is extended or adjusted under 35 U.S.C. 154(b) by 337 days.

(21) Appl. No.: 14/790,626

(22) Filed: Jul. 2, 2015

(51) Int. Cl.
| | |
|---|---|
| *G10K 15/00* | (2006.01) |
| *G01N 29/30* | (2006.01) |
| *G01N 29/07* | (2006.01) |
| *G01N 29/26* | (2006.01) |

(52) U.S. Cl.
CPC ............. *G01N 29/30* (2013.01); *G01N 29/07* (2013.01); *G01N 29/262* (2013.01)

(58) Field of Classification Search
CPC .. G01N 27/904; G01N 29/262; G01N 27/902; G01N 27/90; G01N 2291/2675; G01N 29/30; G01N 2291/2634; G01N 2291/267; G01N 27/9006; G01N 27/9033; G01N 29/043; G01N 29/4463; G01N 2291/2638

See application file for complete search history.

(56) References Cited

U.S. PATENT DOCUMENTS

| | | | |
|---|---|---|---|
| 8,521,446 B2 | 8/2013 | Zhang et al. | |
| 2012/0130653 A1* | 5/2012 | Zhang | G01N 29/069 702/56 |

* cited by examiner

*Primary Examiner* — Robert Bachner
(74) *Attorney, Agent, or Firm* — C. Tricia Liu

(57) ABSTRACT

The method of validating a calibration of a phased-array inspection instrument uses a calibration block having two reflectors located below an inspection surface at two different depths. The method comprises: obtaining angle reference data associating expected angles with corrected angles, each corrected angle being usable to propagate a phased-array beam into the calibration block at a true angle relative to the inspection surface that corresponds to the corresponding expected angle; propagating, from the inspection surface and targeting each one of the two reflectors, phased-array beams into the calibration block at a true angle using the angle reference data, and measuring echo signals associated with the propagated phased-array beams; determining time-of-flight values corresponding to the reflection of the phased-array beams on the two reflectors using the echo signals; and validating the calibration of the phased-array inspection instrument using the time-of-flight values, the two different depths and the true angle.

21 Claims, 6 Drawing Sheets

METHOD OF CALIBRATING A PHASED ARRAY ULTRASONIC SYSTEM WITHOUT KNOWN TEST OBJECT SOUND SPEED

FIELD

The improvements generally relate to the field of nondestructive testing (NDT) and more particularly to the field of phased-array ultrasonic testing (PAUT).

BACKGROUND

For years now, ultrasonic waves (i.e. high frequency acoustic waves) have been used to detect cracks, voids, porosity, and other internal discontinuities hidden in solid material such as metals, composites, plastics, and ceramics, as well as to measure thickness and analyze solid material properties. For instance, phased-array (PA) ultrasonic testing is an inspection technique which is known to be non-destructive, safe and, by now, well-established in the manufacturing, process, and service industries.

For instance, a typical PA inspection instrument generally comprises a probe and an inspection unit for operating the probe upon given parameters which can depend on the type of material of a test object to inspect, the geometry of the test object to inspect and/or the conditions in which inspection is to be performed. The typical probe includes an array of ultrasonic acoustic transducers which two main functions are, during use, to transmit time-shifted acoustic pulses in order to propagate a phased-array beam in the test object to inspect and to receive echo signals resulting from the propagation of the transmitted phased-array beams in the test object. Each acoustic pulse is time-shifted such that the individual acoustic pulses arrive in phase at a focal point after being refracted at an interface between the probe and the test object. Upon reception, the operating inspection unit is configured to display the received echo signals in a manner which allows a user to identify and localize flaws that may or may not exist in the inspected test object, for instance.

In use, however, the user may desire to inspect the test object using a phased-array beam having a propagation axis forming a given expected angle relative to the test object to inspect. To do so, the user inputs the expected angle in the PA inspection instrument which computes, using Snell's law of refraction, propagation instructions indicating how the acoustic transducer elements are to be collectively operated in order to propagate the requested phased-array beam. However, since the coupling efficiency of one acoustic pulse in the test object depends on its incident angle relative to the test object and on the acoustic velocity in the test object, not all the time-shifted acoustic pulses are evenly coupled in the test object, which can cause a bias (also referred to as "Snell's disparities") between the requested phased-array beam and the phased-array beam truly propagated in the test object. More specifically, the phased-array beam actually propagated in the test object may form a biased angle relative to the test object rather than forming the expected angle. Such a bias can prevent the user from suitably positioning the flaws that may be present in the inspected test object, which can, in turn, cause time and cost inefficiencies.

To circumvent the challenge associated with the uneven coupling efficiency, U.S. Pat. No. 8,521,446 B2 to Zhang et al. proposes a method of calibrating the PA inspection instrument which compensates for the bias caused by the uneven coupling efficiency by measuring actual, true angles of the phased-array beams propagating in the test object to inspect using a calibration procedure. The proposed calibration procedure typically requires the user to perform high-precision, perhaps encoded, measurements using a reference block having fixed geometric and physical characteristics such as a precisely known acoustic velocity. Although appropriate in controlled conditions (e.g. in laboratories), this calibration procedure requires a degree of precision which is difficult to achieve on the field which may result in poor calibration of the phased-array inspection unit. There thus remains room for improvement.

SUMMARY

There is provided a system and method of validating a calibration of a phased-array (PA) inspection instrument using a calibration block having two reflectors located below an inspection surface at two different depths.

Broadly described, the method involves a step of obtaining angle reference data for calibrating the PA inspection instrument. The angle reference data can be used to compensate for the bias caused by the uneven coupling of the acoustic pulses in the test object to inspect. The angle reference data may be previously determined, in controlled conditions, using a reference block that has a reference acoustic velocity.

Calibrating the PA inspection instrument using the angle reference data may or may not be appropriate depending on the circumstances. So, validating the calibration of the PA inspection instrument with the angle reference data using the calibration block is required. In an aspect, the PA inspection instrument is used to position the two reflectors of the calibration block and to estimate a depth difference separating the two reflectors, assuming an acoustic velocity of the calibration block which is in the same range as the reference acoustic velocity of the reference block. If the estimated depth difference substantially corresponds to the actual depth difference between the two reflectors, the calibration of the PA inspection instrument can be deemed acceptable. However, if the estimated depth difference differs from the actual depth difference between the two reflectors, the calibration of the PA inspection instrument can be deemed faulty. In such a situation, the acoustic velocity of the calibration block is corrected to render the estimated depth difference similar to the actual depth difference. When properly validated by the method and system described herein, the calibration of the PA inspection instrument can provide satisfactory identification and localization of defects within the test object.

In accordance with one aspect, there is provided a method of validating a calibration of a phased-array inspection instrument using a calibration block having at least two reflectors located below an inspection surface at two different depths, the method comprising the steps of: obtaining angle reference data for calibrating the phased-array inspection instrument, the angle reference data associating expected angles with corrected angles, each corrected angle being usable to propagate a given phased-array beam into the calibration block at a given true angle relative to the inspection surface that corresponds to a corresponding expected angle; propagating, from the inspection surface and into the calibration block, at least one phased-array beam targeting one of the reflectors and at least one phased-array beam targeting the other one of the reflectors, each phased-array beam being propagated at a true angle relative to the inspection surface using the angle reference data, and measuring at least two echo signals associated with the at least two propagated phased-array beams; for each one of the two reflectors, determining a time-of-flight value corresponding to the reflection of the at least one phased-array beam on the reflector; and validating the calibration of the phased-array inspection instrument based on the at least two time-of-flight values, the two different depths and the true angle.

In accordance with another aspect, there is provided a phased-array inspection instrument comprising: a probe; a phased-array inspection unit configured to operate the probe to propagate phased-array beams in a calibration block having two reflectors located below an inspection surface at two different depths, the phased-array inspection unit having a processor and a computer-readable memory, the computer-readable memory being configured for obtaining angle reference data for calibrating the phased-array inspection instrument, the angle reference data associating expected angles with corrected angles, each corrected angle being usable to propagate a given phased-array beam into the calibration block at a given true angle relative to the inspection surface that corresponds to an expected angle, the computer-readable memory being configured for storing computer-readable instructions that when executed by the processor perform the steps of: propagating, into the calibration block, at least one phased-array beam targeting one of the reflectors and at least one phased-array beam targeting the other one of the reflectors, each phased-array beam being propagated at a true angle relative to the inspection surface using the angle reference data; measuring at least two echo signals associated with the at least two propagated phased-array beams; for each one of the two reflectors, determining a time-of-flight value corresponding to the reflection of the at least one phased-array beam on the reflector; and validating the calibration of the phased-array inspection instrument based on the at least two time-of-flight values, the two different depths and the true angle.

In accordance with another aspect, there is provided a computer program product for validating a calibration of a phased-array inspection instrument, the computer software product comprising: a computer-readable memory configured for obtaining angle reference data for calibrating the phased-array inspection instrument, the angle reference data associating expected angles with corrected angles, each corrected angle being usable to propagate a given phased-array beam into the calibration block at a given true angle relative to the inspection surface that corresponds to a corresponding expected angle; the computer-readable memory being configured for storing computer-readable instructions that when executed by a processor perform the steps of: determining a first time-of-flight value using a first echo signal measured in response of a first phased-array beam being propagated, from the inspection surface of the calibration block, at one of the true angles relative to the inspection surface and targeting the first reflector of the calibration block; determining a second time-of-flight value using a second echo signal measured in response of a second phased-array beam being propagated, from the inspection surface of the calibration block, at one of the true angles relative to the inspection surface and targeting the second reflector of the calibration block; and validating the calibration of the phased-array inspection instrument based on the first and second time-of-flight values, the two different depths and the one of the true angles.

As will be understood, the step of validating the calibration of the PA instrument broadly can include calculating an acoustic velocity of the calibration block, estimating a depth difference associated with two reflectors of the calibration block, correcting the angle reference data, generating an output signal, the latter indicating that the calibration is satisfactory or not, etc.

Many further features and combinations thereof concerning the present improvements will appear to those skilled in the art following a reading of the instant disclosure.

DESCRIPTION OF THE FIGURES

In the figures.

These drawings depict exemplary embodiments for illustrative purposes, and variations, alternative configurations, alternative components and modifications may be made to these exemplary embodiments.

DETAILED DESCRIPTION

Figure 1:
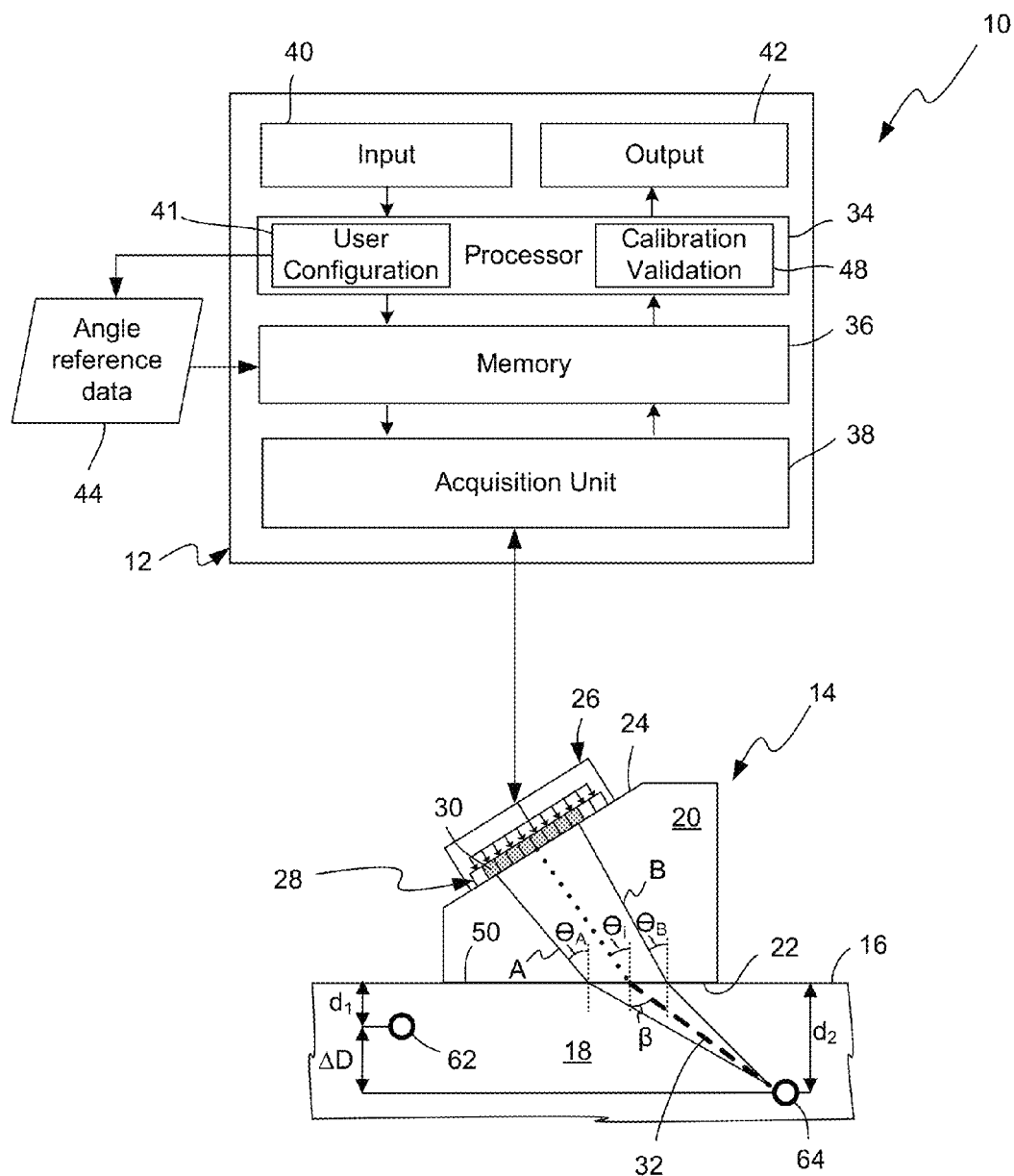
FIG. 1 is a schematic view of a phased-array (PA) inspection system, in accordance with an embodiment.

FIG. 1 shows a schematic view of a phased-array (PA) inspection instrument 10 having an inspection unit 12 and a probe 14 disposed on an inspection surface 16 of a calibration block 18, in accordance with an embodiment. The inspection unit 12 is configured to operate the probe 14 to propagate phased-array beams into the calibration block 18 (or any test object) and to measure echo signals in response to the propagated phased-array beams.

The probe generally has a wedge 20 having a base portion 22 to be disposed on the inspection surface 16 of the calibration block 18, or the inspection surface of a test object 54 (see FIGS. 2A-B), and an upper inclined surface 24 which is adapted to receive a PA probe 26. The inspection unit 12 is generally configured for operating the probe 14 upon given parameters which can vary from an inspection to another. The PA probe 26 includes an array 28 of ultrasonic acoustic transducers 30 whose two main functions are, during use, to transmit time-shifted acoustic pulses in order to propagate a phased-array beam (illustrated as path 32) in the calibration block 18 and to receive echo signals resulting from the propagation of the transmitted phased-array beams therein.

As shown in FIG. 1, the inspection unit 12 has a processor 34, a memory 36, an acquisition unit 38, an input 40 and an output 42. In an embodiment, the PA inspection instrument 10 is configured for obtaining angle reference data 44 and for storing the angle reference data 44 on the memory 36 in such a way that the angle reference data 44 are used by the processor 34 in order to calibrate the PA inspection instrument 10. As mentioned above, such calibration helps compensating for the uneven coupling of the acoustic pulses into the calibration block 18. The processor 34 contains information about a user configuration 41, which may include type of probe, type of wedge, type of acoustic transducers or apertures, focal laws, focal depths, type of material and its nominal acoustic velocity. Information about user configuration 41 is transmitted to angle reference data 44, so that the angle reference data may be customized according to the user configuration 41.

The processor 34 also includes a calibration validation module 48 configured to measure at least two echo signals associated with at least two propagated phased-array beams, to determine a time-of-flight value for each one of the two reflectors, corresponding to the reflection of at least one phased-array beam on the reflector, and to validate the calibration of the phased-array inspection instrument based on at least two time-of-flight values, the two different depths and the true angle.

The angle reference data 44 typically associate each one of a plurality of expected angles $\beta_s$ with a corresponding one of a plurality of corrected angles $\beta_s^*$, wherein each corrected angle $\beta_s^*$ is usable to propagate a given phased-array beam into the calibration block 18 at a given true angle $\beta$ relative to the inspection surface 16 (e.g. relative to a normal of the inspection surface) that corresponds to the expected angle $\beta_s$. More specifically, a PA inspection instrument which is not calibrated, or only poorly calibrated, with the angle reference data 44 mentioned above may suffer from the uneven coupling of the acoustic pulses at the interface between the probe and the calibration block (referred to as "probe-block interface" 50) or at the interface between the probe and a test object 54 to be inspected (referred to as "probe-object interface" 52 shown in FIGS. 2A-B). Indeed, the coupling efficiency of the acoustic pulses depend on their own incidence angle relative to the probe-block interface 50. For instance, referring back to FIG. 1, path A associated with an acoustic pulse emitted from a leftmost one of the array 28 of acoustic transducer elements 30 forms a different incidence angle than path B associated with an acoustic pulse emitted from a rightmost one of the array 28 of acoustic transducer elements 30 (i.e. θA≠θB). Each acoustic pulse is time-shifted from one another such that the individual acoustic pulses arrive in phase at a focal point after being refracted at the probe-block interface 50. Such time-shifts are calculated by the inspection unit 12 using Snell's law of refraction between an incidence angle θi of an in-wedge phased-array beam (illustrated as the dotted portion of path 32) relative to the probe-block interface 50 and an expected angle $\beta$ of an in-object phased-array beam (illustrated as the dashed portion of path 32). These calculations typically receive an input provided in the form of the expected angle $\beta_s$ at which a phased-array beam is requested to propagate in the calibration block 18 or in the test object 54. The inspection unit 12 then determines propagation instructions, i.e. how the acoustic transducer elements 30 are to be operated, to propagate the in-wedge phased-array beam in a manner that yields an in-block (or in-object) phased-array beam having the expected angle $\beta^*$ once refracted at the probe-block interface 50.

Figure 2A:
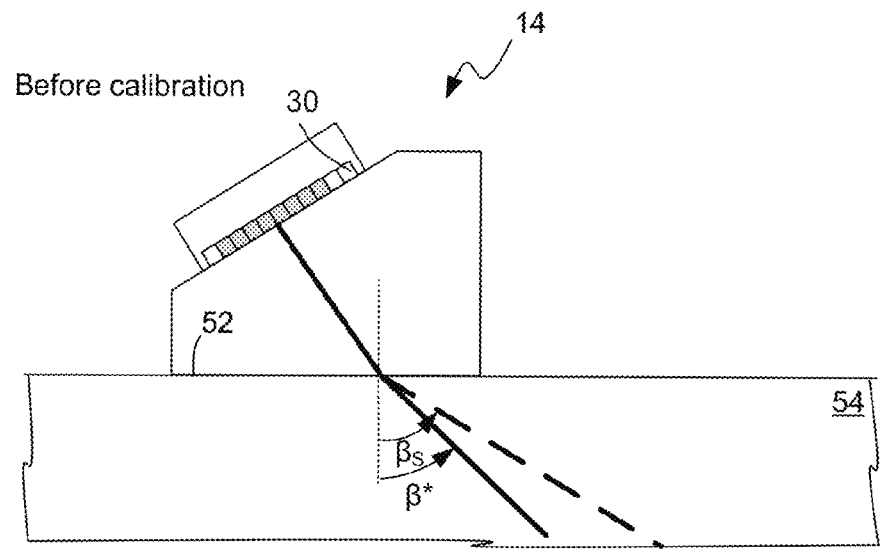
FIG. 2A is a side view of a probe of a PA inspection instrument disposed on a test object, before calibration using angle reference data.

Consequently, before the calibration of the PA inspection instrument using the angle reference data 44, as depicted in FIG. 2A, if a user requests the propagation of a given phased-array beam at the expected angle $\beta_s$ relative to the probe-object interface 52, the inspection unit uses the expected angle $\beta_s$ in Snell's refraction law calculations to determine propagating instructions indicating how each one of the acoustic transducers 30 are to be operated to cause a phased-array beam to be propagated at expected angle $\beta_s$. However, due to the uneven coupling of the acoustic pulses at the probe-object interface 52, the given phased-array beam tends to be refracted at a mere biased angle $\beta^*$ which does not correspond to the expected angle $\beta_s$.

Figure 2B:
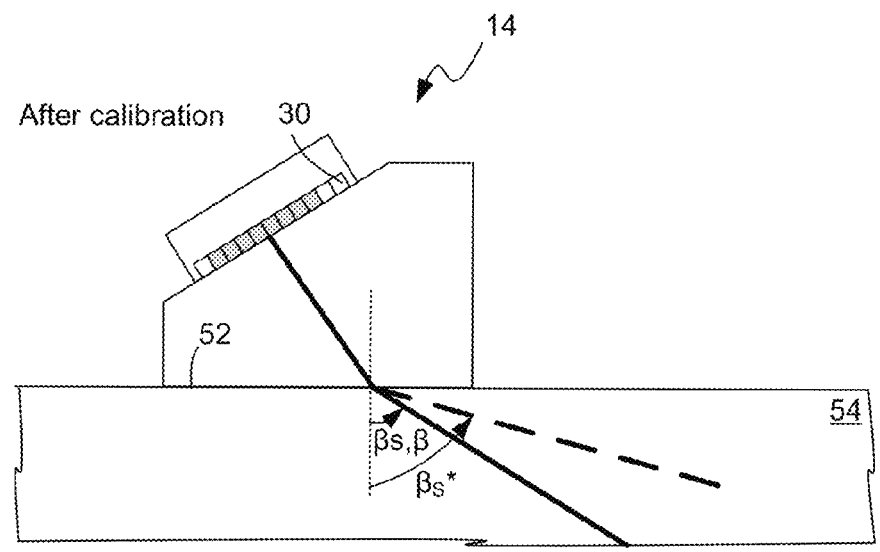
FIG. 2B is a side view of a probe of a PA inspection instrument disposed on a test object, after calibration using angle reference data.

After the calibration of the PA inspection instrument 10 using the angle reference data 44, as shown in FIG. 2B, if the user requests the propagation of the given phased-array beam at the expected angle $\beta_s$ relative to the probe-object interface 52 to a PA inspection instrument 10 calibrated with the angle reference data 44, the PA inspection instrument 10 uses the angle reference data 44 to determine corrected propagation instructions which cause the phased-array beam to be refracted at a true angle $\beta$ which corresponds to the expected angle $\beta_s$. More specifically, the PA inspection instrument 10 determines the corrected propagation instructions by using the corrected angle $\beta_s^*$ in Snell's refraction law calculations, the latter being associated with the expected angle $\beta_s$ with the angle reference data 44.

Figure 3:
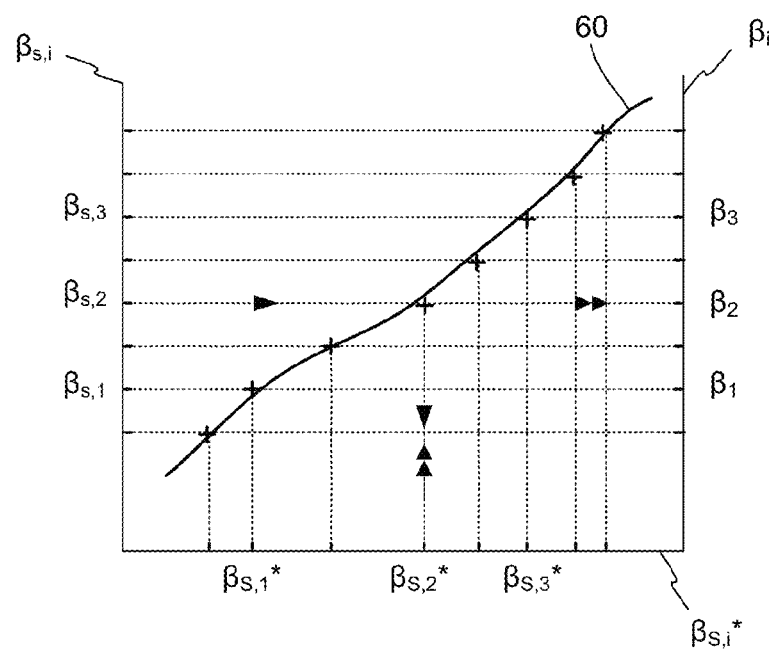
FIG. 3 is a graph showing a calibration curve associating expected angles with true angles, in accordance with an embodiment.

FIG. 3 shows an example of the angle reference data 44, in accordance with an embodiment. As shown, the angle reference data 44 is provided in the form of a calibration curve 60 which associates the expected angles $\beta_{s,i}$ with the corrected angles $\beta_{s,i}^*$ to obtain true angles $\beta_i$ which correspond to the expected angles $\beta_{s,i}$, where i is a positive integer. In another embodiment, the angle reference data 44 can be provided in the form of a look-up table, or any other suitable form. In use, the inspection unit 12 receives a request for propagating a given phased-array beam at the expected angle $\beta_{s,2}$, the PA inspection instrument 10 uses the angle reference data to determine the corrected angle $\beta_{s,2}^*$ associated with the expected angle $\beta_{s,2}$, as depicted by single-headed arrows. The inspection unit 12 then uses the corrected angle $\beta_{s,2}^*$ in the Snell's refraction law calculations in order to determine the corrected propagation instructions which yield the given phased-array beam propagating at the true angle $\beta_2$ which corresponds to the requested, expected angle $\beta_{s,2}$, as illustrated by the two-headed arrows, for instance.

It will be understood that performing measurements with a PA inspection instrument which is not calibrated, or which is poorly calibrated, is to be avoided in the field. Consequently, since the angle reference data 44 which are used to calibrate the PA inspection instrument can be previously determined, for instance, in a controlled environment such as a PA inspection instrument manufacturer's laboratory, the user will want to validate the calibration of the PA inspection instrument 10 before using the instrument in the field. In order to validate the calibration of the PA inspection instrument 10, the user employs the calibration block 18, as will be detailed hereunder.

Referring back to FIG. 1, the method of validating disclosed herein involves the use of the calibration block 18. The calibration block 18 has two reflectors, i.e. a first reflector 62 and a second reflector 64, located below the inspection surface 16 of the calibration block 18 at two different depths, i.e. a first depth $d_1$ and a second depth $d_2$. The calibration block 18 is thus characterized by a depth difference $\Delta D$ which corresponds to the subtraction of the first depth to the second depth, or vice versa, depending on which reflector is deeper so that the depth difference is a positive value (e.g. $\Delta D=d_2-d_1$). In the illustrated embodiment, the depth difference $\Delta D$ is given by $d_2$ minus $d_1$, for instance. As shown, each reflector is provided in the form of a side-drilled hole (SDH) having a given diameter. Still, the reflectors 62 and 64 can be any other suitable type of homogeneous reflectors. For instance, the calibration block 18 can be a NAVSHIPS block. The calibration block 18 typically has a nominal acoustic velocity $V_0$ which can be known only to a limited precision. Moreover, the calibration block 18 is typically different from the reference block with which the angle reference data 44 have been determined, for instance, using the method proposed in U.S. Pat. No. 8,521, 446 B2 to Zhang et al. Although different, the reference block is generally made of a material having acoustic properties relatively similar to those of the calibration block 18 (e.g. acoustic velocities in the same range of order). Since the angle reference data 44 may have been previously determined in an environment different from the environment in which the PA inspection instrument 10 is to be used, the user will prefer to validate the calibration of the PA inspection instrument 10 in the field using the calibration block 18. Without this step of validating, the acoustic velocity in the calibration block 18 is assumed to be the nominal acoustic velocity $V_0$. However, the nominal acoustic velocity $V_0$ of the calibration block 18 can differ from the actual acoustic velocity of the calibration block 18. Using the nominal acoustic velocity $V_0$ can perhaps cause the PA inspection instrument 10 to yield unsatisfactory measurements.

Figure 4:
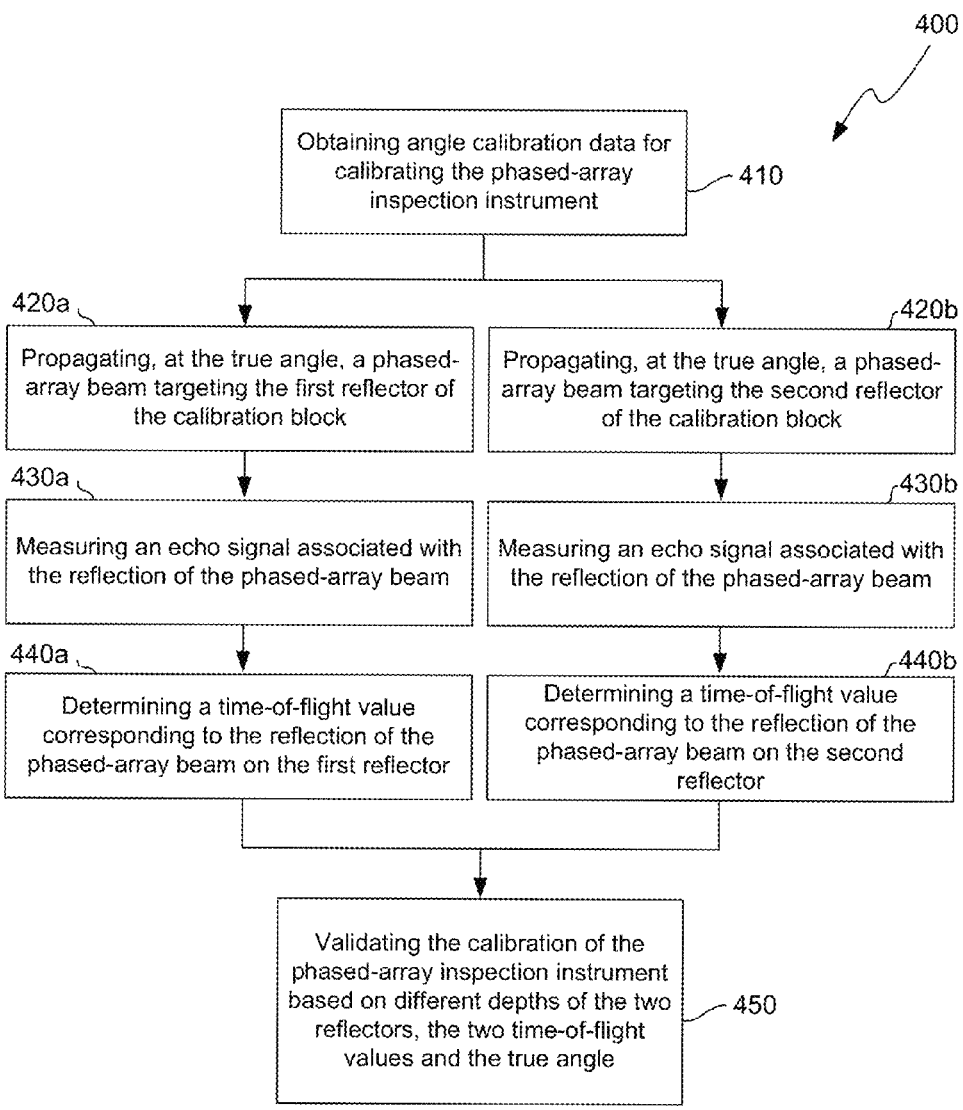
FIG. 4 is a flowchart of an example of a method of validating a calibration of a PA inspection instrument, in accordance with an embodiment.

FIG. 4 is a flowchart of an exemplary method 400 of validating the calibration of the PA inspection instrument 10, in accordance with an embodiment. As depicted, the method has a step of obtaining the angle reference data 44 for calibrating the PA inspection instrument 10 at 410. In an embodiment, the angle reference data 44 are stored on the memory 36 of the PA inspection instrument 10 for access by the processor 34 at any moment deemed suitable. In another embodiment, the angle reference data 44 are stored on an external memory (e.g. a memory stick) which is to be coupled directly to the PA inspection instrument 10. In still another embodiment, the angle reference data 44 are obtained indirectly using a network linking the PA inspection instrument 10 to the angle reference data 44 stored on a database of the PA inspection probe's manufacturer. In another embodiment, the step of obtaining the angle reference data 44 is limited to the angle reference data 44 relevant to a given inspection configuration. Indeed, the angle reference data to be obtained in step 410 depend on the inspection configuration chosen by the user of the PA inspection instrument 10. For instance, the angle reference data 44 can depend on a type of probe, a type of wedge, a type of acoustic transducers or apertures, given focal laws, a given focal depth, a type of material, a nominal acoustic velocity $V_0$, etc. Obtaining the angle reference data 44 associated with only a given inspection configuration can be convenient since obtaining angle reference data 44 associated with all the possible inspection configurations is typically burdensome.

Figure 5A:
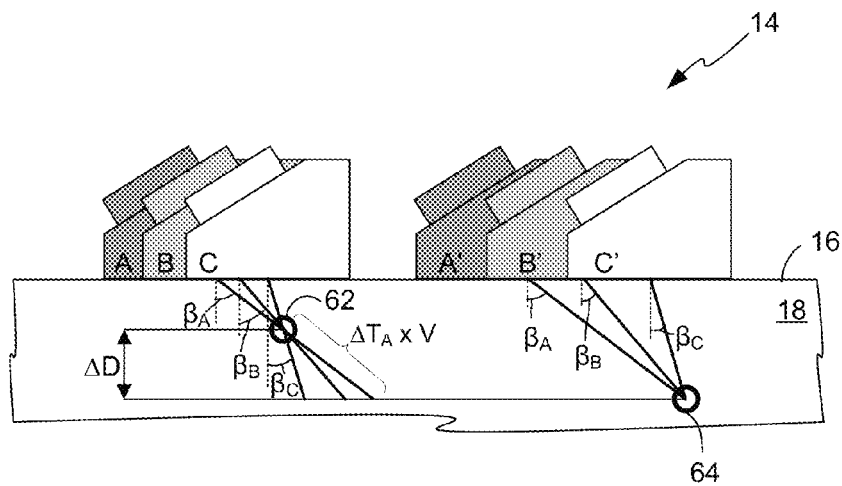
FIG. 5A is a side view of a probe of a PA inspection instrument disposed at a plurality of positions along an inspection surface of a calibration block, in accordance with an embodiment.

The method 400 involves the use of the calibration block 18 at steps 420a through 430b. Using the calibration block 18, the PA inspection instrument 10 is used to propagate, from the inspection surface 16 of the calibration block 18 and targeting the first reflector 62 at depth $d_1$, at least one phased-array beam in the calibration block 18 at a true angle $\beta_i$ (corresponding to an expected angle $\beta_{s,i}$) using the angle reference data 44 at 420a, and measuring a corresponding echo signal at 430a. The PA inspection instrument 10 is further used to propagate, from the inspection surface 16 and targeting the second reflector 64 at depth $d_2$, at least one phased-array beam in the calibration block 18 at the true angle $\beta_i$ using the angle propagation data 44 at 420b, and measuring a corresponding echo signal at 430b. Each of the echo signals is then used to determine time-of-flight values $t_1$ and $t_2$ corresponding to the reflection of the phased-array beams regarding, respectively, the first reflector 62 at $d_1$ and the second reflector 64 at $d_2$ at 440a and 440b. The time-of-flight values $t_1$ and $t_2$ can be subtracted from one another to obtain a time-of-flight difference $\Delta T$ (e.g. $\Delta T=t_2-t_1$) which is indicative of the period of time that would be required for a given phased-array beam, when propagating at the true angle $\beta_i$, to propagate from the first reflector 62 to the second reflector 64 in the calibration block 18 (with respect to a factor two in this case). The time-of-flight difference $\Delta T$ is typically a positive value so that the time-of-flight difference $\Delta T$ has the same polarity as the depth difference $\Delta D$. If the nominal acoustic velocity $V_0$ of the calibration block 18 is appropriate, the product of the time-of-flight difference $\Delta T$ and the nominal acoustic velocity $V_0$ of the calibration block 18 (i.e. $\Delta T \times V_0$) trigonometrically corresponds to the hypotenuse of a right triangle having a cathetus corresponding to the depth difference $\Delta D$, as shown in FIG. 5A. The method 400 has a step of validating the calibration of the PA inspection instrument based on the first and the second depths $d_1$ and $d_2$, the two time-of-flight values $t_1$ and $t_2$ and the true angle $\beta_i$, as shown at 450.

Figure 5B:
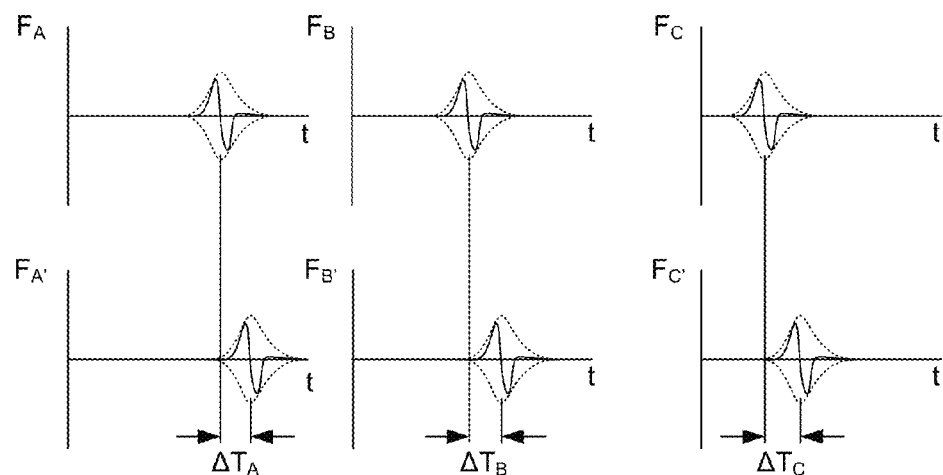
FIG. 5B shows graphs of exemplary echo signals associated with phased-array beams propagated into the calibration block from the plurality of positions shown in FIG. 5A.

As illustrated in FIGS. 5A-B, the method disclosed herein can use more than one true angles $\beta_i$ to validate the calibration of the PA inspection instrument 10. More specifically, FIG. 5A is a side view showing the probe 14 positioned at exemplary positions A, A', B, C and C' along the inspection surface 16 and over the first and the second reflectors 62 and 64. When the probe 14 is disposed at positions A, A', the probe interrogates the two reflectors 62 and 64 with a true angle $\beta_A$. When the probe 14 is disposed at positions B, B', the probe 14 interrogates the two reflectors 62 and 64 with a true angle $\beta_B$. When the probe 14 is disposed at positions C, C', the probe 14 interrogates the two reflectors 62 and 64 with a true angle $\beta_C$. In another embodiment, each reflector is interrogated from a plurality of positions at a plurality of true angles $\beta_i$. FIG. 5B show typical echo signals $F_i$ resulting from the propagation of the phased-array beams targeting the first reflector 62 ($F_A$, $F_B$, and $F_C$) and the second reflector 64($F_A'$, $F_B'$, and $F_C'$). In this embodiment, a time-of-flight difference $\Delta T_i$ is determined for the positions A, A', the positions B, B', and the positions C, C' to obtain time-of-flight differences $\Delta T_A$, $\Delta T_B$ and $\Delta T_C$. Each time-of-flight value is determined relative to a reference temporal position of an envelope of the measured echo signal. For instance, in the illustrated echo signals shown in FIG. 5B, the reference temporal position is a maximum value of the envelope. As it will be detailed below, the method can use the plurality of time-of-flight differences $\Delta T_i$ to validate the calibration of the PA inspection instrument 10.

In an embodiment, the step of validating involves calculating a true acoustic velocity $V_0'$ of the calibration block 18 based on the one or more time-of-flight difference $\Delta T_i$, the two different depths and the one or more true angle $\beta_i$. For instance, the true acoustic velocities $V_{0,i}'$ can be given by the actual depth difference $\Delta D$ divided by the time-of-flight difference $\Delta T_i$ and divided by the cosine of the true angle $\beta_i$, that is:

$$V'_{0,i} = \frac{\Delta D}{\Delta T_i \cos \beta i}. \quad (1)$$

In this specific embodiment, the PA inspection instrument 10 can use an average of the true acoustic velocities $V_{0,i}'$ for further measurements.

In another embodiment, the step of validating involves calculating an estimated depth difference $\Delta D_i'$ given by the product of the time-of-flight difference $\Delta T_i$ (see example in FIG. 6A), the nominal acoustic velocity $V_0$ of the calibration block 18 and the cosine of the true angle $\beta_i$, that is:

$$\Delta D_i' = \Delta T i \times V_0 \times \cos \beta_i. \quad (2)$$

In this embodiment of the method, when the estimated depth difference $\Delta D_i'$ substantially corresponds to the actual depth difference $\Delta D$, the PA inspection instrument 10 is configured to generate an output signal which indicates that the nominal acoustic velocity of the calibration block is satisfactory. The nominal acoustic velocity is deemed satisfactory when it corresponds to the actual depth difference $\Delta D$ with respect to a tolerance value such as a relatively small positive or negative constant.

If it is determined that the estimated depth difference $\Delta D_i'$ does not correspond to the actual depth difference $\Delta D$ of the calibration block 18, the calibration of the PA inspection instrument 10 and the nominal acoustic velocity $V_0$ are deemed not satisfactory. In this situation, the PA inspection instrument 10 is configured to generate an output signal which indicates that the calibration of the PA inspection instrument 10 is not satisfactory. In such a situation, the PA inspection instrument 10 is configured to correct the nominal acoustic velocity of the calibration block 18.

Figure 6A:
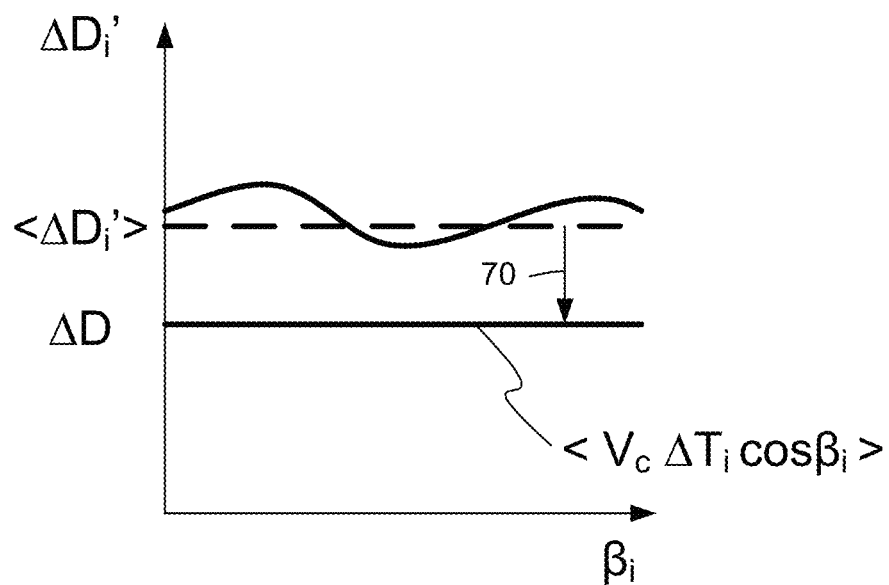
FIG. 6A is a graph showing an example of estimated depth differences with respect to true angles, in accordance with an embodiment.

FIG. 6A shows an example of a graph of the estimated depth difference $\Delta D_i'$ as a function of the true angle $\beta_i$ resulting from measurements taken by a user on the field, for instance. In this example, the average of the estimated depth difference $\langle \Delta D_i' \rangle$ does not correspond to the actual depth difference $\Delta D$. Accordingly, the PA inspection instrument 10 is configured to calculate a corrected acoustic velocity $V_c$ of the calibration block 18 such that the average of the estimated depth differences $\langle \Delta D_i' \rangle$ corresponds to the depth difference $\Delta D$ with respect to the tolerance value (see arrow 70). Depending on the circumstances, the validation of the calibration of the PA inspection system 10 involves the use of the corrected acoustic velocity $V_c$ for subsequent measurements using the PA inspection system 10.

Figure 6B:
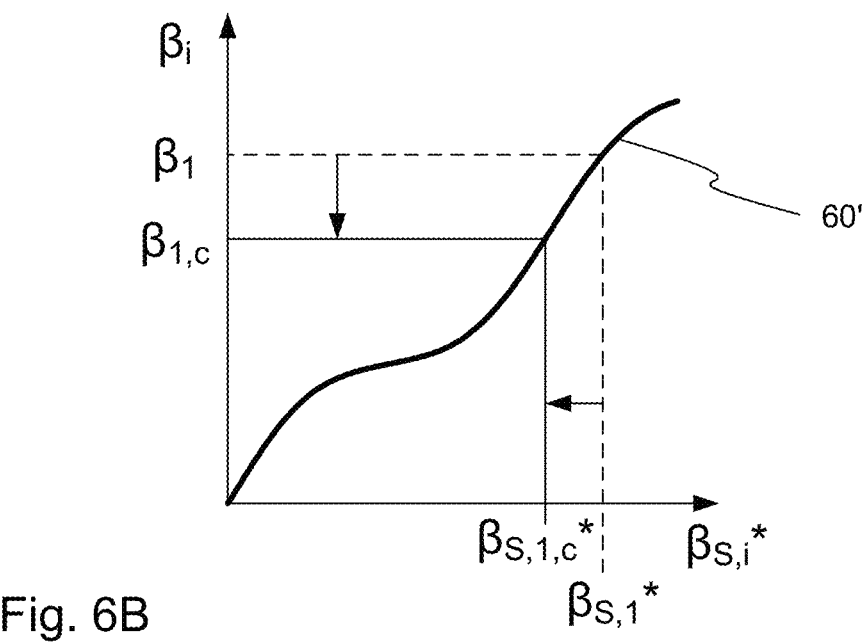
FIG. 6B shows a graph showing a calibration curve associating corrected angles with true angles, in accordance with an embodiment.

In another embodiment, the validation of the PA inspection instrument 10 involves further steps. Indeed, since the uneven coupling of the acoustic pulses into the calibration block 18 depends on the incident angle $\theta i$ of each one of the acoustic pulses but also depends on the acoustic velocity of the calibration block 18, correcting the angle reference data 44 can be deemed appropriate. FIG. 6B shows angle reference data 44 provided in the form of a calibration curve 60' which associates each one of a plurality of corrected angles $\beta_{s,i}*$ with a corresponding one of a plurality of true angles $\beta_i*$. It is assumed that the angle reference data 44 are substantially invariant with respect to the acoustic velocity of the calibration block 18 and/or the test object 54. In an embodiment, when a corrected acoustic velocity $V_c$ has been determined, the PA inspection instrument 10 can correct the angle reference data 44. In this embodiment, correcting the angle reference data 44 involves shifting the corrected angles $\beta_{s,i}*$ towards new corrected angle $\beta_{s,i,c}*$ to determine new true angles $\beta_{1,c}$ using the corrected acoustic velocity $V_c$ and the calibration curve 60. More specifically, shifting the corrected angles $\beta_{s,i}*$ can be performed by calculating the new corrected angle $\beta_{s,i,c}*$ for each corrected angle $\beta_{s,i}*$ by solving for $\beta_{s,i,c}*$ in the following Snell's law of refraction equation:

$$\frac{\sin\beta_i}{V_w} = \frac{\sin\beta_{s,i,c}*}{V_c}. \quad (3)$$

Still referring to FIG. 6B, the corrected angle $\beta_{s,1}*$ is shifted towards $\beta_{s,1,c}*$ using equation (3) which yields the new true angle $\beta_{1,c}$. In this embodiment, the PA inspection instrument 10 is configured to estimate, yet again, the depth difference $\Delta D_i'$ but using the corrected angle reference data in an iterative manner. At the end of each iteration, if it is determined that the newly estimated depth difference $\Delta D_i'$ still does not sufficiently correspond to the depth difference $\Delta D$, the PA inspection instrument 10 is configured to calculate a new corrected acoustic velocity of the calibration block 18 and to re-correct the already corrected angle reference data and so forth.

In another embodiment of the method of validating the PA inspection instrument 10, the inspection unit 12 is configured to output an output signal which indicates that the angle reference data are not appropriate when the estimated depth difference $\Delta D_i$ is not substantially constant for all the true angles $\beta_i$ measured. Indeed, if it is determined that even after calibration of the PA inspection instrument 10 using the angle reference data 44, the estimated depth difference $\Delta D_i$ for each of the true angles $\beta_i$ differs substantially from one another (e.g. yielding a line having a significant slope or a higher order curve), it may be preferred to advise the user that the calibration is not validated and that the user may acquire its own angle reference data in order to calibration the PA inspection instrument 10.

In another embodiment, the step of validating includes a validation of a wedge delay (WD) associated with the probe 14 of the PA inspection instrument 10. Validating the wedge delay associated with the probe can use one of the time-of-flight values $t_1$ and $t_2$, at least one of the two different depths $d_1$ and $d_2$ and the true angle $\beta$. Indeed, in some circumstances, the wedge 20 of the probe 14 can wear (e.g. deteriorate) which can result in a wedge 20 having a reduced height compared to a nominal height of the wedge 20 used for determining the angle reference data 44. For instance, the wedge delay can be computed by the following equation:

$$WD(\beta) = t_i - \frac{2d_i}{Vc\cos\beta}. \quad (4)$$

In this situation, it can be useful to modify the angle reference data 44 and the focal laws with respect to the wedge delay thereafter.

In an embodiment, the angle reference data are obtained from a previously determined full matrix capture (FMC) database. The FMC database comprises a plurality of FMC associated with a multitude of inspection configurations (various reference blocks, types of wedges, types of probes, acoustic transducers or apertures, focal laws, focal depths, different types of materials, differing nominal acoustic velocities, and the like). Each FMC results from a data-acquisition process which is preferably performed in controlled conditions. Determining a FMC requires that each acoustic transducer element 30 is used as the transmitter while all the other acoustic transducer elements 30 are used as receivers in order to obtain the FMC containing all the received signals. For a given inspection configuration, the angle reference data 44 can be precisely determined from the FMC by producing a synthetic reference data acquisition following the exact inspection configuration of the operator.

In another embodiment, the angle reference data 44 are previously determined manually by a skilled operator for each of a plurality of inspection configurations. In other words, the angle reference data 44 for a given inspection configuration will involve measuring the true angles using a specific reference block, using a specific wedge, a specific type of probe and so forth. When performed for a plurality of inspection configurations, the manually determined angle reference data 44 can be combined to form a main database. During use, the PA inspection instrument may only obtain angle reference data 44 associated with one inspection configuration rather than obtaining the whole main database.

In another embodiment, the angle reference data result from a simulation obtained by a suitable simulation program. The simulation program simulates a virtual PA probe, a virtual wedge and a virtual reference block in order to determine the angle reference data that is to be applied to a given inspection configuration in order to propagate phased-array beams at true angles $β_i$. For instance, the simulation program is run on a computer of a PA inspection instrument's manufacturer in order to yield angle reference data which are obtained by the inspection unit 12 at a moment deemed suitable. The simulation program can be stored on the memory 36 and can be run in real-time by the processor 34 in order to generate the angle reference data 44 upon reception of a request.

As can be understood, the examples described above and illustrated are intended to be exemplary only. For instance, the inspection surface 16 may be curved or wavy to an appropriate extent which allows the methods and systems described herein to suitably determine the corrected angles. Moreover, other trigonometric relations can be used to validate the PA inspection instrument 10. For instance, when the angles β are measured with respect to the inspection surface 16, rather than a normal of the inspection surface 16, using the sinus of the angle may be more appropriate than using the cosine. Further, the reference block (either real or actual) and the calibration block can have more than two reflectors, the method and system disclosed are not limited to only two or more reflectors. Indeed, validating the calibration of the PA inspection instrument 10 using more than two reflectors in the calibration block can be seen fit in some circumstances. Angle-correction gain (ACG) and time-correction gain (TCG) may apply as one having ordinary skills in the art may appreciate. The scope is indicated by the appended claims.

What is claimed is:

1. A method of validating a calibration of a phased-array inspection instrument using a calibration block having at least two reflectors located below an inspection surface at two different depths having a true depth difference therebetween, the method comprising the steps of:
    obtaining angle reference data for calibrating the phased-array inspection instrument, the angle reference data associating expected angles with corrected angles, each corrected angle being usable to propagate a given phased-array beam into the calibration block at a given true angle relative to the inspection surface that corresponds to a corresponding expected angle;
    propagating, from the inspection surface and into the calibration block, at least one phased-array beam targeting one of the reflectors and at least one phased-array beam targeting the other one of the reflectors, each phased-array beam being propagated at a true angle relative to the inspection surface using the angle reference data, and measuring at least two echo signals associated with the at least two propagated phased-array beams;
    for each one of the two reflectors, determining a time-of-flight value corresponding to the reflection of the at least one phased-array beam on the reflector;
    validating the calibration of the phased-array inspection instrument by estimating an estimated depth difference based on the at least two time-of-flight values, a nominal acoustic velocity of the calibration block and the true angle; and
    generating an output signal indicating that the difference between the estimated depth difference and the true depth difference is less than a tolerance value.

2. The method of claim 1, wherein the angle reference data are previously determined using a reference block having a reference acoustic velocity, the reference block being made of a material having acoustic properties substantially similar to that of the calibration block.

3. The method of claim 1, wherein the angle reference data are obtained from a full matrix capture (FMC) database.

4. The method of claim 1, wherein the step of propagating and the step of determining are performed using two or more of the true angles to obtain two or more differences of time-of-flight values, wherein said validating is further based on the two or more differences of time-of-flight values.

5. The method of claim 1, wherein said validating further comprises calculating an acoustic velocity of the calibration block based on the at least two time-of-flight values, the two different depths and the true angle.

6. The method of claim 5, wherein said calculating the acoustic velocity of the calibration block is given by the true depth difference divided by a difference of the two time-of-flight values and divided by the cosine of the true angle, the resulting acoustic velocity being a positive value.

7. The method of claim 1, wherein said validating further comprises generating the output signal indicating that the nominal acoustic velocity of the calibration block is satisfactory when the estimated depth difference corresponds to the true depth difference with respect to the tolerance value.

8. The method of claim 1, wherein said validating further comprises, when the estimated depth difference does not correspond to the true depth difference with respect to the tolerance value,
    calculating a corrected acoustic velocity of the calibration block such that the estimated depth difference corresponds to the true depth difference with respect to the tolerance value; and
    correcting the angle reference data based on the corrected acoustic velocity and calibrating the phased-array inspection instrument using the corrected angle reference data.

9. The method of claim 8, wherein the steps of estimating the estimated depth difference, calculating the corrected acoustic velocity and correcting the angle reference data are iteratively performed until the estimated depth difference corresponds to the true depth difference with respect to the tolerance value.

10. The method of claim 1, wherein the step of validating further comprises validating a wedge delay associated with a probe of the phased-array inspection instrument using at least one of the time-of-flight values, at least one of the two different depths and the true angle.

11. A phased-array inspection instrument comprising:
a probe;
a phased-array inspection unit configured to operate the probe to propagate inspection phased-array beams in a calibration block having two reflectors located below an surface at two different depths having a true depth difference therebetween, the phased-array inspection unit comprises,
a computer-readable memory, the computer-readable memory being further configured for storing computer-readable instructions,
an output signal configured to indicate when the calibration is validated;
a processor including a user configuration module being configured to obtain angle reference data for calibrating the phased-array inspection instrument, the angle reference data associating expected angles with corrected angles, each of the corrected angles being usable to propagate a given phased-array beam into the calibration block at a given true angle relative to the inspection surface that corresponds to a corresponding expected angle, wherein the processor is configured to cause propagation into the calibration block of at least one phased-array beam targeting one of the reflectors and at least one phased-array beam targeting the other one of the reflectors, each phased-array beam being propagated at the corresponding true angle relative to the inspection surface using the angle reference data,
wherein the processor further comprises a calibration validation module configured to measure at least two echo signals associated with the at least two propagated phased-array beams, to determine a time-of-flight value for each one of the two reflectors, corresponding to the reflection of the at least one phased-array beam on the reflector,
to validate the calibration of the phased-array inspection instrument by estimating an estimated depth difference based on the at least two time-of-flight values, a nominal acoustic velocity of the calibration block and the true angle; and,
to activate the output signal when the difference between the estimated depth difference and the true depth difference is less than a tolerance value.

12. The phased-array inspection instrument of claim 11, wherein the calibration block is a side-drilled hole (SDH) block.

13. The phased-array inspection instrument of claim 11, wherein the angle reference data are previously determined using a reference block having a reference acoustic velocity, the reference block being made of a material having acoustic properties substantially similar to a material of the calibration block.

14. The phased-array inspection instrument of claim 11, wherein the angle reference data are obtained from a full matrix capture (FMC) database.

15. The phased-array inspection instrument of claim 11, wherein the calibration validation module determines two or more of the true angles to obtain two or more differences of time-of-flight values, and validates the calibration based on the two or more differences of time-of-flight values.

16. The phased-array inspection instrument of claim 11, wherein the calibration validation module is further configured to calculate an acoustic velocity of the calibration block based on the at least two time-of-flight values, the two different depths and the true angle.

17. The phased-array inspection instrument of claim 16, wherein the calibration validation module is further configured to calculate the acoustic velocity of the calibration block by the true depth difference divided by a difference of the two time-of-flight values and divided by the cosine of the true angle, the resulting acoustic velocity being a positive value.

18. The phased-array inspection instrument of claim 11, wherein the calibration validation module further generates the output signal indicating that the nominal acoustic velocity of the calibration block is satisfactory when the estimated depth difference corresponds to the true depth difference with respect to the tolerance value.

19. The phased-array inspection instrument of claim 11, wherein, when the estimated depth difference does not correspond to the true depth difference with respect to the tolerance value, the calibration validation module:
calculates a corrected acoustic velocity of the calibration block such that the estimated depth difference corresponds to the true depth difference with respect to the tolerance value; and
corrects the angle reference data based on the corrected acoustic velocity and calibrates the phased-array inspection instrument using the corrected angle reference data.

20. The phased-array inspection instrument of claim 11, wherein the calibration validation module iteratively estimates the estimated depth difference, calculates a corrected acoustic velocity and corrects the angle reference data, continuing to iterate until the estimated depth difference corresponds to the true depth difference with respect to the tolerance value.

21. A computer program product for validating a calibration of a phased-array inspection instrument, the computer software product comprising:
a computer-readable memory configured for obtaining angle reference data for calibrating the phased-array inspection instrument, the angle reference data associating expected angles with corrected angles, each corrected angle being usable to propagate a given phased-array beam into the calibration block at a given true angle relative to the inspection surface that corresponds to a corresponding expected angle; the computer-readable memory being configured for storing computer-readable instructions that when executed by a processor perform the steps of:
determining a first time-of-flight value using a first echo signal measured in response of a first phased-array beam being propagated, from the inspection surface of the calibration block, at one of the true angles relative to the inspection surface and targeting the first reflector of the calibration block;
determining a second time-of-flight value using a second echo signal measured in response of a second phased-array beam being propagated, from the inspection surface of the calibration block, at one of the true angles relative to the inspection surface and targeting the second reflector of the calibration block;
validating the calibration of the phased-array inspection instrument by calculating an estimated depth difference based on the first and second time-of-flight values, a nominal acoustic velocity of the calibration block and the one of the true angles; and, generating an output signal indicating that the difference between the estimated depth difference and the true depth difference is less than a tolerance value.

\* \* \* \* \*